United States Patent [19]

Sellers

[11] Patent Number: 5,295,492

[45] Date of Patent: Mar. 22, 1994

[54] DEVICE FOR CONNECTING A GUIDEWIRE TO AN EXTENSION GUIDEWIRE

[75] Inventor: James M. Sellers, Haverhill, Mass.

[73] Assignee: C. R. Bard, Inc., Murray Hill, N.J.

[21] Appl. No.: 959,045

[22] Filed: Oct. 9, 1992

[51] Int. Cl.$^5$ ............................................... A61B 5/00
[52] U.S. Cl. ........................................................ 128/772
[58] Field of Search ............... 128/657, 772; 604/95, 604/282, 283; 403/220, 221, 223, 292

[56] References Cited

U.S. PATENT DOCUMENTS

| | | | |
|---|---|---|---|
| 2,586,581 | 2/1992 | Tschischeck. | |
| 3,944,328 | 3/1976 | Kent et al. | 350/96 C |
| 4,448,478 | 5/1984 | Matthews et al. | 350/96.21 |
| 4,594,121 | 6/1986 | Mitch | 156/158 |
| 4,636,033 | 1/1987 | Gagen | 350/96.21 |
| 4,687,470 | 8/1987 | Okada | 604/171 |
| 4,707,068 | 11/1987 | Moulin | 350/96.21 |
| 4,712,862 | 12/1987 | Lightstone | 350/96.21 |
| 4,726,369 | 2/1988 | Mar | 128/657 |
| 4,799,496 | 1/1989 | Hargreaves et al. | 128/772 |
| 4,860,742 | 8/1989 | Park et al. | 604/159 |
| 4,875,489 | 10/1989 | Messner et al. | 128/657 |
| 4,907,332 | 3/1990 | Christian et al. | 29/237 |
| 4,958,642 | 9/1990 | Christian et al. | 128/772 |
| 4,961,433 | 10/1990 | Christian | 128/772 |
| 4,973,329 | 11/1990 | Park et al. | 606/1 |
| 5,109,867 | 5/1992 | Twyford | 128/772 |
| 5,113,872 | 5/1992 | Jahrmarkt et al. | 128/772 |
| 5,117,838 | 6/1992 | Palmer et al. | 128/772 |
| 5,133,364 | 7/1992 | Palermo et al. | 128/772 |
| 5,135,535 | 8/1992 | Kramer | 604/194 |
| 5,137,512 | 8/1992 | Burns et al. | 604/96 |
| 5,139,032 | 8/1992 | Jahrmarkt et al. | 128/657 |

Primary Examiner—Max Hindenburg
Attorney, Agent, or Firm—Darby & Darby

[57] ABSTRACT

A device and method of use for facilitating the axial connection of small diameter wires, and in particular for connecting a guidewire to an extension guidewire. Using a male/female interconnecting arrangement, the end of a guidewire is connected axially to the end of an extension guidewire using a device having a first body member including a channel or groove located on the upper surface of the first body member, the channel having a cross-section corresponding to that of the larger guidewire and dimensioned slightly wider so that the guidewires are in a sliding fit in the channel; and a second body member dimensioned to fit over the first body member as a cover, the second body member having a transparent portion located over the channel, the transparent portion being curved throughout its length to effect magnification and provide visual assistance thereof. The guidewires are placed end to end in the channel under the transparent magnifying portion so that positioning and aligning the guidewires to axially interconnect the male and female connectors of the guidewires can be done quickly and easily.

25 Claims, 2 Drawing Sheets

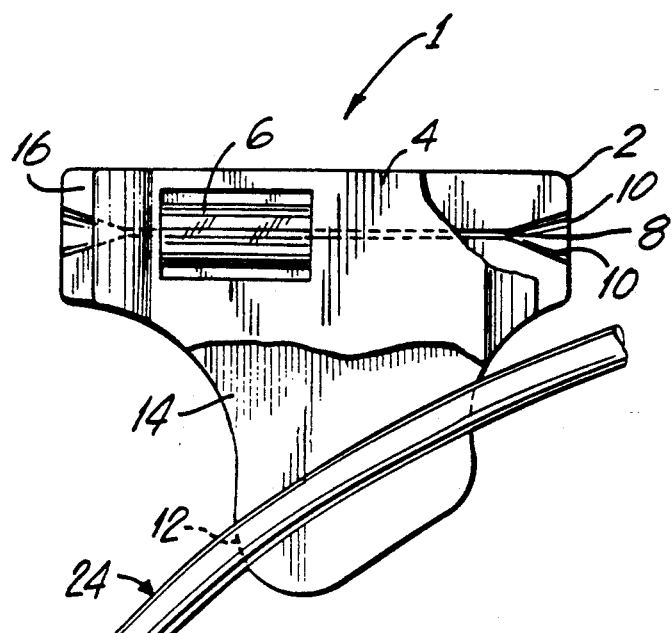
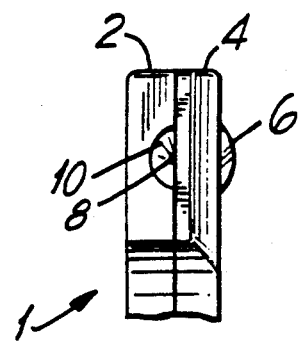
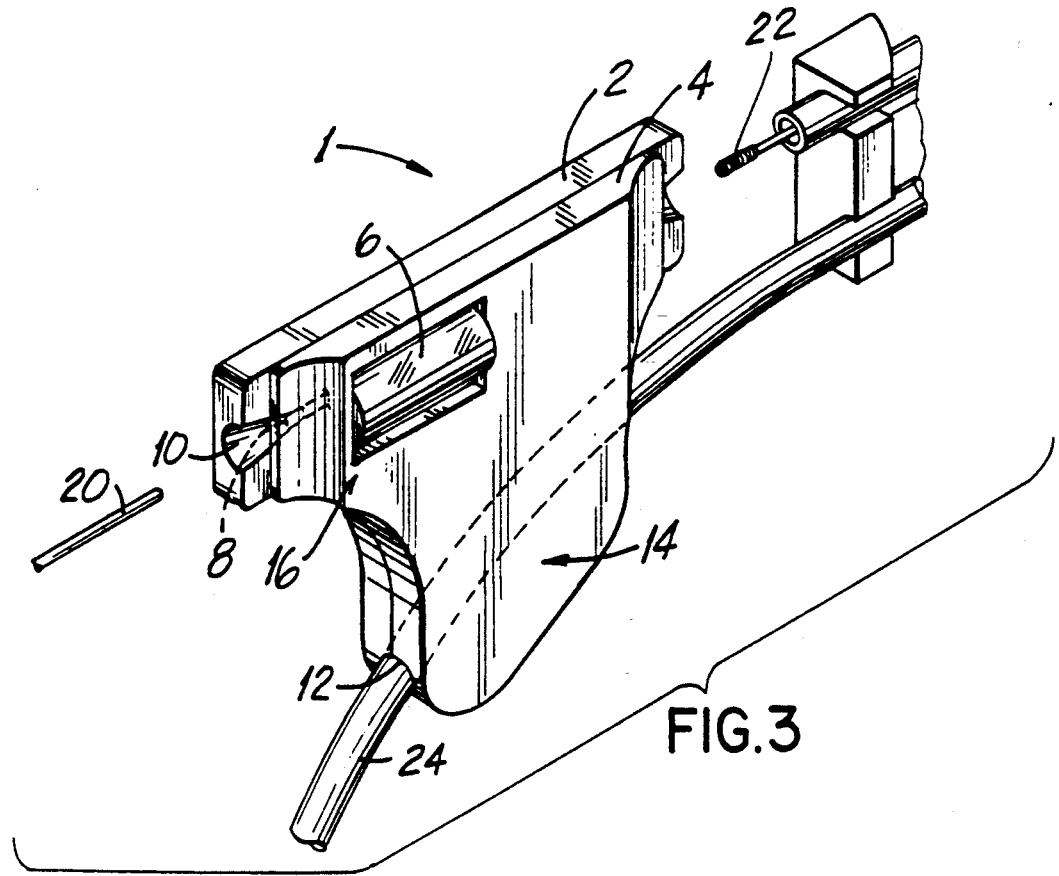

DEVICE FOR CONNECTING A GUIDEWIRE TO AN EXTENSION GUIDEWIRE

FIELD OF THE INVENTION is invention relates generally to guidewires for use in cardiovascular surgical procedures, and more particularly to the procedure for connecting a guidewire to a guidewire extension.

BACKGROUND OF THE INVENTION

Guidewires are routinely used in medical procedures where a catheter is introduced into a patient's arteries or veins. In cardiovascular procedures such as angioplasty and valvuloplasty, a guidewire is inserted by a physician into the patient's blood vessel and advanced until the distal end of the guidewire reaches the location to be treated. Once the guidewire is placed, a catheter is slid over the guidewire and advanced until it is positioned with its distal end at the diseased location within the patient.

In certain cases the in-situ catheter may be changed during the cardiovascular procedure. For example, a physician may use several balloon dilatation catheters having balloons of progressively increasing size to unblock a stenosis in the patient's artery. It is important to perform the catheter exchange without moving the position of the guidewire from the location to be treated so that the guidewire can be used to direct the new catheter to the same location.

One method of exchanging catheters is to attach one end of an extension guidewire to the proximal end of the in-situ guidewire and withdraw the catheter over the extension guidewire while leaving the in-situ guidewire in place. A new catheter can then be advanced over the coupled guidewires, and the extension guidewire can be disconnected after the new catheter is placed at the location to be treated within the patient's blood vessel. The two guidewires are typically attached using a female connector on the end of one guidewire and a male connector on the one end of the other guidewire, the interconnection of which can be releasably secured.

With respect to guidewires used in coronary artery catheterization, a major disadvantage with the interfitting connectors is that they have very small diameters, which makes positive alignment of the coupling extremely difficult to see and accomplish under the conditions in which these procedures are performed. Moreover, the length of an extension guidewire is typically in the order of 125 cm., which makes its handling somewhat awkward when a physician or attendant is attempting to align the proximal end of the in-situ guidewire with the end of the extension guidewire. As a result of these difficulties, the procedure of connecting an extension guidewire to an in-situ guidewire is tedious, painstaking, time consuming and has some risk of guidewire movement or improper alignment of the in-line connection involved. All of this adds to the spiralling cost of medical procedures using guidewires and catheters.

Thus, there is a need for a device and method, heretofore unavailable, which provides visual assistance while facilitating the positive alignment of a small diameter guidewire and an extension guidewire, when connecting their ends together.

Accordingly, it is an object of the present invention to provide a device which has a guidewire alignment channel and a magnifying media positioned thereover, for facilitating the end-to-end connection of a small diameter guidewire and an extension guidewire placed therein.

It is another object of the present invention to provide a method of connecting a guidewire to a guidewire extension by positioning the end of the guidewire and the end of the extension guidewire in-line to each other in a confined space that contains a magnifying media positioned thereover so that a positive connection of the two wires can be achieved quickly and easily.

It is still another object to provide a device for connecting a guidewire to a guidewire extension that is simple in design and use, and economical to manufacture.

The foregoing objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

In accordance with the objects of the present invention, a brief summary of an exemplary embodiment is presented. Some simplifications and omissions may be made in the following summary, which is intended to highlight and introduce some aspects of the present invention, but not to limit its scope. Detailed descriptions of an exemplary embodiment adequate to allow those of ordinary skill in the art to make and use the inventive concepts will be provided later.

According to a broad aspect of the invention, a device is provided for connecting by an axial movement a small diameter wire and an extension wire, having a male connection member on the one wire and a female connection member on the other wire comprising a first body member having a channel extending from the outer surface longitudinally of the first body member, the channel having a width only slightly greater than the largest wire diameter; a second body member in comparative relationship with the first body member and positioned so as to avoid interference with the wire, including axial movement thereof within the channel; and a transparent magnifying means positioned on one of the body members in a position to permit viewing of the channel for positioning and manipulating the wires, to permit an interconnection between the male and female connectors of the wires.

The invention also provides for a method of connecting a wire to an extension wire—one having a male connecting member, the other having a female connecting member including positioning the wire and the extension wire with the male connecting member and female connecting member in full relationship within a confined space only slightly larger than the diameter of the largest wire; providing a transparent magnifying means in a position to observe the confined space; advancing the male connector member and female connector member towards one another; using the transparent magnifying means while advancing the wires to adjust the position of the wires to insure axial alignment;

and causing the wires to be connected together by axial movement.

BRIEF DESCRIPTION OF THE DRAWINGS

FIG. 1 is a front view of a guidewire connecting device, illustrating one embodiment of the present invention.

FIG. 2 is a side view of a guidewire connecting device, illustrating one embodiment of the present invention.

FIG. 3 is a perspective view of a guidewire connecting device assembled with a guidewire packaging hoop.

DETAILED DESCRIPTION OF A PREFERRED EMBODIMENT

Figure 4:
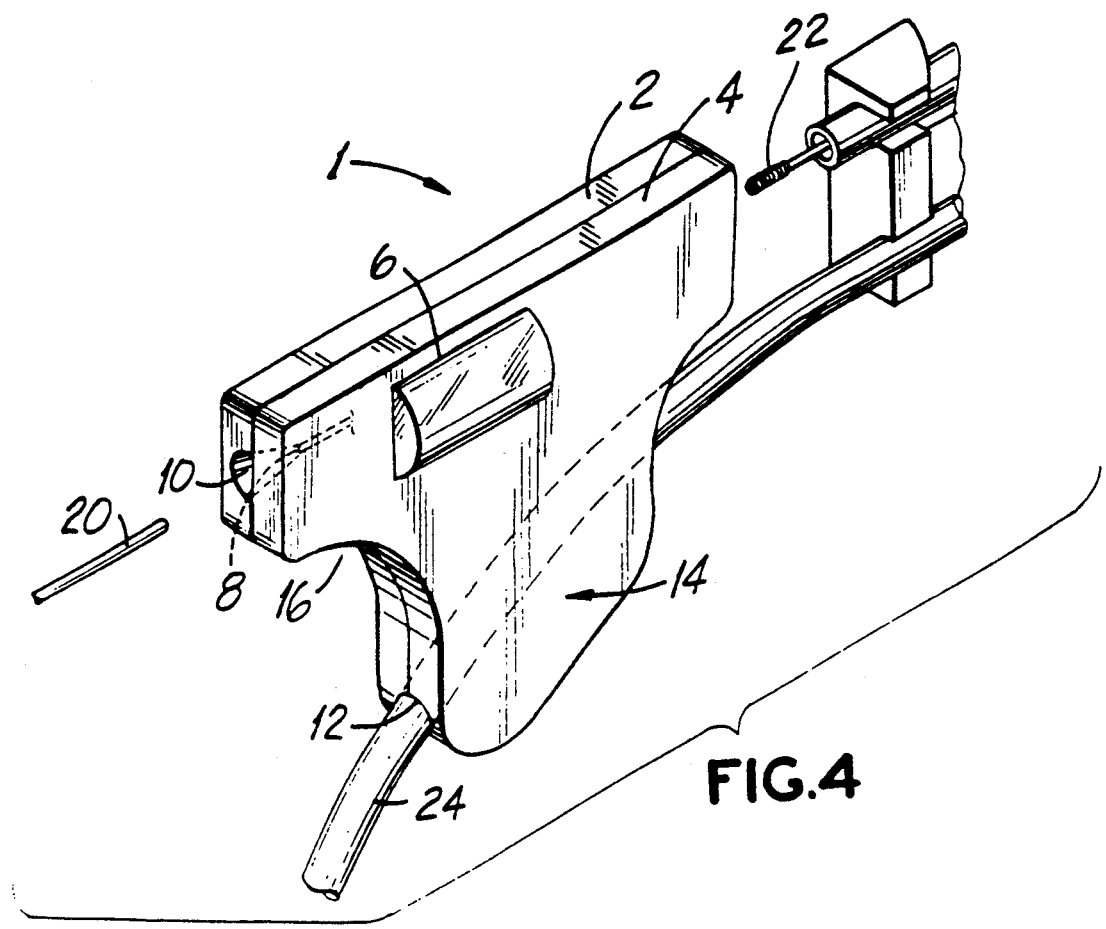
FIG. 4 is a perspective view illustrating an additional embodiment of a guidewire connecting device assembled with a guidewire packaging hoop.

The present invention contemplates a device for facilitating the axial connection of the end of a guidewire to an extension guidewire for exchanging catheters during a surgical procedure.

Referring to the drawings, there is illustrated in FIGS. 1-3 one embodiment of the present invention. In FIGS. 1-3, a guidewire connecting tool or introducer 1 according to one embodiment of the present invention is shown.

The guidewire introducer 1 includes a rigid, base planar or first body member 2 that has a substantially rectangular portion 16, and a hand grip portion 14 diverging away from one side of the rectangular portion 16. The handgrip portion 14 is dimensioned and configured to be held comfortably in the hand of a user during normal use of the guidewire introducer 1. In the preferred embodiment, the handgrip portion 14 is integrally formed with the rectangular portion 16, such that the handgrip portion 14 is an extension of the rectangular portion 16. However, the rectangular portion 16 and the handgrip portion 14 may be formed as separate elements that are bonded together by the use of an adhesive, bonding agent, or the like.

The rectangular portion 16 includes a longitudinal groove or through-slit opening 8 that forms a channel along its upper surface 16. The opening 8 traverses from one side of the rectangular portion 16 to the other. As shown in FIGS. 1 and 3, the axis of the opening 8 is substantially perpendicular to the axis of the handgrip portion 14, but not so limited.

For the greater part of its length, the cross-section of the opening 8 is dimensioned slightly larger than that of the diameter of a guidewire 20 (shown in FIG. 3) or of an extension guidewire 22 (also shown in FIG. 3). This enables the guidewire 20 and the extension guidewire 22 to be moved axially in the confined opening 8 by longitudinal sliding movement, while maintaining the ends of the guidewire 20 and the extension guidewire 22 in substantial alignment with each other.

Although it is preferable that the opening 8 be dimensioned as one continuous width, it is possible and perhaps desirable to provide opening 8 with two different widths (not shown), such that one portion of the width of opening 8 corresponds to the diameter of the larger extension guidewire 22 and another portion of the width of opening 8 corresponds to the diameter of the smaller guidewire 20. In this configuration, the opening 8 would step down from the larger width to the smaller width as the opening 8 is traversed, allowing the extension guidewire 22 to be inserted only up to the step between the two widths. This step then acts as a stop when inserting the extension guidewire 22, while the smaller width portion of opening 8 limits the vertical movement of the guidewire 20 so that a more accurate alignment of the guidewires 20, 22 can be quickly achieved.

As shown in FIGS. 1-4, the opening 8 may further include an outwardly tapering portion 10 on each end of the opening 8 (tapering towards the median of opening 8) to facilitate insertion of the respective guidewire 20 and extension guidewire 22 therein.

In the preferred embodiment, the first body member 2 is made from a polycarbonate material having sufficient rigidity. However, it should be noted that the first body member 2 may also be formed from, for example, metal or any of several well-known, suitable plastic materials.

A cover or second body member 4, which is preferably dimensioned to substantially the same size and shape as the first body member 2 but not so limited, has a planar surface that covers the opening 8 without interfering with the axial movement of a guidewire 20 or extension guidewire 22 positioned therein. The second body member 4 acts as a cover to the first body member 2. However, in the preferred embodiment, the second body member 4 does not completely cover the tapering portions 10, and includes concave recessions in its upper surface in the areas adjacent the tapering portions 10. (See FIGS. 1 and 3). This configuration is provided to further facilitate the insertion of the guidewire 20 and the extension guidewire 22 into the opening 8.

The second body member 4 is preferably made from a polycarbonate material having sufficient rigidity. However, like the first body member 2, the second body member 4 may also be formed from metal or any suitable plastic material. The second body member 4 is preferably secured to the first body member 2 by an ultrasonic weld, but it is not so limited in that it may be attached to the first body member 2 by the use of any suitable adhesive, bonding agent, mechanical snap-fit, or the like.

The second body member 4 includes a transparent portion 6 located over the opening 8. In a preferred embodiment, the transparent portion 6 is transversely curved throughout its length to effect magnification. The transparent portion 6 is elongated so as to longitudinally extend over an area of the opening 8 that permits magnified viewing of at least the end connectors of the guidewire 20 and the extension guidewire 22 when placed end-to-end in the opening 8. The width of the transparent portion 6 is preferably greater than the cross-section of the opening 8 so that the entire width of the opening 8 will appear magnified under the transparent portion 6.

It is preferable that the transparent portion 6 be integrally formed with the second body member 4, and recessed therein (as shown in FIGS. 1-3). However, the transparent portion 6 may be integrally formed with the second body member 4, but configured so that it protrudes from the upper surface of the second body member 4 such that the transparent portion 6 is an extension of the second body member 4. See FIG. 4. In either configuration, the transparent portion 6 can alternatively be formed as a separate element which is secured to the second body member 4 by the use of an adhesive, a weld, or any other suitable bonding means.

As illustrated in preferred embodiment in FIGS. 1 and 3, both the first body member 2 and the second body member 4 further include complementary, longitudinal concave indentations in their respective hand grip portions 14 that form an aperture 12 when the upper surface of the first body member 2 and the lower surface of the second body member 4 are secured together to form the guidewire introducer 1. The aperture 12 is an arcuate shaped through-bore that defines an elongated passage for receiving an extension guidewire packaging hoop or container 24 therethrough. The aperture 12 has a configuration and diameter sufficient to maintain the extension guidewire container 24 firmly therein without substantial movement with respect to the guidewire introducer 1.

It is anticipated that the guidewire introducer 1 would be pre-assembled with a packaged extension guidewire 22, such that a portion of the packaging container 24 is securely positioned in the aperture 12, while one end of the extension guidewire 22 is inserted in to one end of the opening 8 and positioned below the transparent portion 6. Assembling the guidewire introducer 1 with a packaged extension guidewire 22 facilitates ready connecting of the extension guidewire 22 and an in-situ guidewire 20 during surgical procedures.

To connect guidewires with the present invention in place, a physician simply inserts the end of the guidewire 20 into one end of the opening 8, and positions it below the transparent portion 6 in axial alignment with the end of the extension guidewire 22 that has been placed in the opposite end of opening 8. It is anticipated that the ends of guidewire 20 and extension guidewire 22 will have some type of suitable complementary male/female coupling arrangement to provide an end-to-end in-line coupling of the two guidewires 20 and 22. For example, see the guidewire extension connector described in U.S. Pat. No. 5,133,364 issued to Palermo et al. and assigned to the assignee herein. It is important to note that the type of axial connector is not critical to the invention, and any suitable axial connective means may also be used.

With the guidewire 20 and the extension guidewire 22 positioned within the opening 8, the connection can be easily made by advancing the guidewires 20 and 22 together while visually insuring proper axial alignment through the assistance of the magnifying transparent portion 6.

After a relatively firm connection is achieved, one which is resistant to axial separation, the guidewire 20 may be held while the guidewire introducer 1 is "stripped" off of the extension guidewire 22 by axially sliding it along the extension guidewire 22. Holding the guidewire introducer 1 firmly by the hand-grip portion 14 while sliding it along the extension guidewire 22 separates it from the container 24 while alleviating the cumbersome handling of an extension guidewire that is currently practiced in the art. Advangateously, the extension guidewire 22 may also be removed from the container 24 by axially withdrawing the guidewire 20 and the connected extension guidewire 22 from the opening 8 while holding the guidewire introducer 1 by the hand-grip portion 14.

The guidewire introducer 1 has been described above in detail with reference to a preferred embodiment that includes the separate elements of a first and second body member 2 and 4, respectively, that are joined together to form the guidewire introducer 1. As may be appreciated by one skilled in the art, it would also be clearly possible and perhaps desirable to form the guidewire introducer 1 from one element such that the second body member 4 carrying the transparent portion 6 is integrally formed with the first body member 2. In this embodiment, the transparent portion 6 would simply be recessed within the upper surface of the guidewire introducer 1, or alternatively, it would simply extend away from the upper surface of the guidewire introducer 1. The opening 8 and the aperture 12 would be through-bores in the guidewire introducer 1.

Moreover, it is important to note that the present invention may be used with equal facility and advantage with other small diameter wire devices that are connected axially, such as, e.g., linear optical fibers. Although the invention has been described in detail with particular reference to a preferred embodiment thereof, it should be understood that the invention is capable of other and different embodiments, and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

I claim:

1. A device for connecting by an axial movement a small diameter wire and an extension wire, having a male connection member on the one wire and a female connection member on the other wire comprising:
    (a) a first body member having a channel extending along an outer surface of said first body member, said channel having a width only slightly greater than the largest wire diameter;
    (b) a second body member in abutting relationship with said first body member and positioned so as to avoid interference with the wire, including axial movement thereof within said channel; and
    (c) a transparent magnifying means positioned on one of said body members in a position to permit viewing of said channel for positioning and manipulating the wires, to permit an interconnection between said male and female connectors of the wires.

2. A device according to claim 1, wherein said channel has two ends and includes a tapered area on each end, said area tapering inward towards the median of said channel to thereby facilitate the insertion of the end of a wire therethrough.

3. A device according to claim 1, wherein said device further includes an aperture for receiving and resiliently holding a container housing at least one of the wires.

4. A device according to claim 3, wherein said aperture is arcuate in shape.

5. A device according to claim 1, wherein said transparent magnifying means is transversely curved throughout its length to effect magnification.

6. A device according to claim 5, wherein said transparent magnifying means is integrally formed as part of said second body member.

7. A method of connecting a wire to an extension wire within a confined space having a dimension only slightly larger than the diameter of the larger of the wires, one of the wires having a male connecting member, the other of the wires having a female connecting member comprising:
    (a) positioning the wire and the extension wire with the male connecting member and female connecting member in full relationship within the confined space;

(b) providing a transparent magnifying means in a position to observe the confined space;

(c) advancing the male connector member and female connector member towards one another;

(d) using the transparent magnifying means while advancing said wires to adjust the position of said wires to insure axial alignment; and (e) causing said wires to be connected together by axial movement.

8. A method according to claim 7, further comprising the step of causing said wires to be removed by axial movement from the confined space.

9. A method according to claim 7, further comprising the step of providing a means for securing a portion of a package containing said extension wire, to facilitate the handling of said extension wire.

10. A device for connecting at least two small diameter guidewires comprising:
   a first body member having a through-slit opening located on the upper surface of said first body member, said through-slit opening having at least part of its cross-section corresponding to the cross-section of the largest of the guidewires and dimensioned slightly wider so that the guidewire may be in a sliding fit in said through-slit opening; and
   a second body member dimensioned to fit over said first body member as a cover, said second body member having a transparent portion located over said through-slit opening, said transparent portion being curved throughout its length to effect magnification.

11. A device according to claim 10, wherein said through-slit opening has two ends and includes a flared taper on each end to facilitate the insertion of the end of a guidewire therethrough.

12. A device according to claim 10, wherein said device further includes a through bore for receiving and resiliently holding a guidewire packaging container.

13. A device according to claim 12, wherein said through-bore is arcuate in shape.

14. A device according to claim 10, further including an integral hand-grip means configured to cup the fingers of a user, for facilitating the grasping and holding of said device.

15. A method of connecting a guidewire to an extension guidewire, one having a male end connector and the other a female end connector, the method comprising the steps of:
   providing a device having a first body member including a longitudinal groove located in the upper surface of said first body member, said groove having a cross-section slightly wider than that of the largest of the guidewires, said device further including a second body member dimensioned to fit over said first body member as a cover, said second body member having a transparent magnifying media located over said groove;
   inserting the female end of one of said guidewire in through one end of said groove;
   inserting the male end of the other of said guidewires in through the other end of said groove;
   advancing each of said guidewires until their respective ends are located below said transparent magnifying media; and
   coupling said guidewires together while positioned under said transparent magnifying media.

16. A method according to claim 15, further comprising the step of causing said guidewires to be removed by axial movement from the said groove.

17. A method according to claim 15, further comprising the step of advancing said device along the length of one of said guidewires until the guidewire has exited said groove.

18. A method according to claim 15, further comprising the step of providing a means for securing a distal area of a package containing said extension guidewire, to facilitate the handling of said extension guidewire.

19. A device for connecting by an axial movement a small diameter wire and an extension wire, having a male connection member on one of the wires and a female connection member on the other of the wires comprising:
   (a) a body member having a channel extending longitudinally across the outer surface of said body member, said channel having a width only slightly greater than the diameter of the largest of the wires; and
   (b) a transparent magnifying means positioned on said body member in a position to permit viewing of said channel member for positioning an manipulating the wires to permit an interconnection between said male and female connectors of the wires, said transparent magnifying means positioned so as to avoid interference with axial movement of the wires within said channel.

20. A device according to claim 19, wherein said channel has two ends and includes a tapered area on each end, said area tapering inward towards the median of said channel to thereby facilitate the insertion of the end of the wire therethrough.

21. A device according to claim 19, wherein said device further includes an aperture for receiving and resiliently holding a container housing at least one of the wires.

22. A device according to claim 21, wherein said aperture is arcuate in shape.

23. A device according to claim 19, wherein said transparent magnifying means is transversely curved throughout its length to effect magnification.

24. A device according to claim 23, wherein said transparent magnifying means is an integrally formed part of said body member.

25. A device according to claim 19, further including a hand-grip means attached thereto for facilitating use of said device.

* * * * *